United States Patent
Ikeda et al.

(10) Patent No.: US 7,737,299 B2
(45) Date of Patent: Jun. 15, 2010

(54) PROCESS FOR PRODUCING 2,2,3,3,-TETRAFLUOROOXETANE

(75) Inventors: Sunao Ikeda, Ibaraki (JP); Takehiro Sonoi, Ibaraki (JP)

(73) Assignee: Unimatec Co., Ltd., Tokyo (JP)

( * ) Notice: Subject to any disclaimer, the term of this patent is extended or adjusted under 35 U.S.C. 154(b) by 0 days.

(21) Appl. No.: 10/589,418

(22) PCT Filed: Feb. 10, 2005

(86) PCT No.: PCT/JP2005/002005

§ 371 (c)(1),
(2), (4) Date: Aug. 15, 2006

(87) PCT Pub. No.: WO2005/080365

PCT Pub. Date: Sep. 1, 2005

(65) Prior Publication Data

US 2007/0191617 A1    Aug. 16, 2007

(30) Foreign Application Priority Data

Feb. 24, 2004    (JP)    ............................ 2004-047915

(51) Int. Cl.
*C07C 59/00*    (2006.01)
(52) U.S. Cl. .................................... 562/586
(58) Field of Classification Search .................. 562/586
See application file for complete search history.

(56) References Cited

U.S. PATENT DOCUMENTS

| 4,886,581 | A | * | 12/1989 | Ohsaka et al. | ................ 203/80 |
| 4,908,460 | A | * | 3/1990 | Ohsaka et al. | .............. 549/511 |
| 4,946,972 | A | * | 8/1990 | Ohsaka et al. | .............. 549/511 |
| 5,519,151 | A | * | 5/1996 | Petrov et al. | ................ 549/510 |
| 6,753,301 | B2 | * | 6/2004 | Howell et al. | ............... 508/582 |
| 7,232,932 | B2 | * | 6/2007 | Howell et al. | ............... 568/615 |

OTHER PUBLICATIONS

Weinmayr, "Hydrogen Fluoride as a Condensing Agent. VI. Reactions of Fluoroolefins with Formaldehyde Hydrogen Fluoride," JOC 28 pp. 492-494 (1963).

* cited by examiner

*Primary Examiner*—Sabiha Qazi
(74) *Attorney, Agent, or Firm*—Brinks Hofer Gilson & Lione

(57) ABSTRACT

In the production of 2,2,3,3-tetrafluorooxethane by reaction of tetrafluoroethylene with a compound of formaldehyde generation source in anhydrous hydrogen fluoride, the reaction is carried out in the presence of polyfluoroalkylcarboxylic acid or polyfluoroalkyl ester thereof, represented by the following general formula RfCOORf' (where Rf is a polyfluoroalkyl group having 1-5 carbon atoms, and Rf' is a hydrogen atom or a polyfluoroalkyl group having 1-5 carbon atoms), preferably $CF_3COOH$, $CF_3COOCH_2CF_2CF_3$, or $CF_3COOCH_2CF_3$, whereby a high reaction yield can be attained.

8 Claims, No Drawings

PROCESS FOR PRODUCING 2,2,3,3,-TETRAFLUOROOXETANE

RELATED APPLICATION

The present application is a 35 U.S.C. 371 national stage filing of International Patent Application No. PCT/JP2005/002005, filed Feb. 10, 2005, through which and to which priority is claimed to Japanese Priority Patent Application No. 2004-047915, filed Feb. 24, 2004.

TECHNICAL FIELD

The present invention relates to a process for producing 2,2,3,3-tetrafluorooxethane, and more particularly to a process for producing 2,2,3,3-tetrafluorooxethane by reaction of tetrafluoroethylene with a compound of formaldehyde generation source in anhydrous hydrogen fluoride.

BACKGROUND ART 2,2,3,3-tetrafluorooxethane is a useful raw material compound for producing fluorine-containing rubber polymers, etc. For example, 2,2,3,3-tetrafluorooxethane can readily undergo polymerization reaction in the presence of an alkali metal halide, and fluorination of the hydrogen atoms of the resulting polyfluoropolyether polymer $F(CH_2CF_2CF_2O)_n CH_2CF_2COF$ by a fluorine gas can give fluorine oil such as perfluoropolyether polymers $F(CF_2CF_2CF_2O)_nCF_2CF_2COF$ or $F(CF_2CF_2CF_2O)_nCF_2CF_3$. React-ion with an alkali metal halide can give a 2,2-difluoropropionic acid derivative represented by the following general formula as raw materials for producing fluorine-containing rubber polymers:

$XCH_2CF_2COF$ (X: Cl, Br or I)

It is known that 2,2,3,3-tetrafluorooxethane having such effective uses can be produced by reaction of tetrafluoroethylene with a compound of formaldehyde generation source in anhydrous hydrogen fluoride.

Patent Literature 1: JP-B-2-37904

It is also reported that 2,2,3,3-tetrafluorooxethane can be obtained as a by-product in the production of 2,2,3,3,3-pentafluoropropanol $CF_3CF_2CH_2OH$ by reaction of tetrafluoroethylene with formaldehyde in anhydrous hydrogen fluoride, but only in a small amount because it is a by-product, and thus cannot be used as raw materials in the industrial scale.

Non-Patent Literature 1: J. Org. Chem. 28, 492-4(1963)

DISCLOSURE OF THE INVENTION

Problem to be Solved by the Invention

An object of the present invention is to provide a process for producing 2,2,3,3-tetrafluorooxethane by reaction of tetrafluoroethylene with a compound of formaldehyde generation source in anhydrous hydrogen fluoride in a high reaction yield.

Means for Solving the Problem

The object of the present invention can be attained by conducting above-mentioned process for producing 2,2,3,3-tetrafluorooxethane in the presence of polyfluoroalkylcarboxylic acid or polyfluoroalkyl ester thereof, represented by the following general formula:

$RfCOORf'$ (where Rf is a polyfluoroalkyl group having 1-5 carbon atoms, and Rf' is a hydrogen atom or a polyfluoroalkyl group having 1-5 carbon atoms).

Effect of the Invention

In the process for producing 2,2,3,3-tetrafluorooxethane by reaction of tetrafluoroethylene with a compound of formaldehyde generation source in anhydrous hydrogen fluoride, the reaction is carried out in the presence of polyfluoroalkylcarboxylic acid or polyalkyl ester thereof, where-by the reaction yield can be enhanced to approximately twice or higher, amounting to nearly 40%.

BEST MODES FOR CARRYING OUT THE INVENTION 2,2,3,3-tetrafluorooxethane can be produced by charging a compound of formaldehyde generation source and polyfluoroalkylcarboxylic acid or polyfluoroalkyl ester thereof into anhydrous hydrogen fluoride, and then adding tetrafluoroethylene thereto. As a compound of formaldehyde generation source, formaldehyde itself can be used, but owing to handling difficulty such as easy polymerizability of formaldehyde, etc., its polymers such as paraformaldehyde, trioxane, etc. can be preferably used. Generation of formaldehyde from the polymers can be carried out by acid decomposition, thermal decomposition etc. Since hydrogen fluoride is involved in the reaction system, acid decomposition based on hydrogen fluoride can be commonly used.

Anhydrous hydrogen fluoride for use in the reaction acts to conduct acid decomposition of the formaldehyde polymer and also as a solvent, and thus can be used in a proportion 1.0-20 equivalent weights, preferably 5-15 equivalent weights to number of moles in terms of HCHO of the formaldehyde polymer. Polyfluoroalkylcarboxylic acid or polyfluoroalkyl ester thereof can be used in a proportion of about 0.05 to about 10 equivalent weights, preferably about 0.2 to about 1.0 equivalent weight to number of moles in terms of HCHO of the formaldehyde polymer.

As the polyfluoroalkylcarboxcylic acid or polyfluoroalkyl ester thereof represented by the afore-mentioned general formula, trifluoroacetic acid $CF_3COOH$, 2,2,3,3,3-pentafluoropropyltrifluoroacetic acid ester $CF_3COOCH_2CF_2CF_3$ and 2,2,2-trifluoroethyltrifluoroacetic acid ester $CF_3COOCH_2CF_3$ can be preferably used. In addition thereto, the following compounds can be also used:

$CF_3CF_2COOH$ $CF_3CF_2COOCH_2CF_2CF_3$ $CF_3CF_2COOCH_2CF_3$ $CF_3CF_2CF_2COOH$ $CF_3CF_2CF_2COOCH_2CF_2CF_3$ $CF_3CF_2CF_2COOCH_2CF_3$ $CF_3CF_2CH_2COOH$ $CF_3CF_2CH_2COOCH_2CF_3$

The reaction can be carried out initially by charging anhydrous hydrogen fluoride, formaldehyde polymer and polyfluoroalkylcarboxylic acid or polyfluoroalkyl ester thereof, and then by adding tetrafluoroethylene thereto. The reaction can be carrier out either under the normal pressure of under super atmospheric pressure. In the case of the normal pressure, tetrafluoroethylene is discharged to the outside of the system, whereby the tetrafluoroethylene-based yield will be lowered. Thus, the flow rate of tetrafluoroethylene must be limited, and the reaction requires much time. The reaction is thus carried out under super atmospheric pressure, usually under about 0.1 to about 2MPa.

The lower the reaction temperature, the lower the reaction rate and the higher the amount of by-product, resulting in a decrease of the yield. On the other hand, the higher the reaction temperature, the more often the decomposition of the desired product, resulting in a decrease of the yield. Thus, it is appropriate to conduct the reaction at a temperature of usually about 0° to about 100° C., preferably about 30° to about 60° C.

EXAMPLES

The present invention will be described in detail below, referring to Examples.

Example 1

800 g of trifluoroacetic acid and 500 g of paraformaldehyde as HCHO source were charged into an autoclave having a capacity of 10 L, and 2.9 kg of anhydrous hydrogen fluoride was changed therein with stirring. Then, heating was carried out, and when the inside temperature reached to 50° C., tetrafluoroethylene [TFE] was added thereto under pressure of 0.88 MPa. As soon as TFE was charged, the inside temperature was elevated and the autoclave inside pressure was lowered. During the reaction, TFE was continuously added thereto portion-by-portion by a compressor to keep the inside pressure at 0.88 MPa. When 1.1 kg of TFE was charged, the portion-by-portion addition was stopped and then ageing was carried out for 12 hours. After ageing, the content was distilled off into a cooling trap at −20° C., followed by alkali neutralization and water washing, whereby 1,130 g of crude product was obtained.

As a result of NMR analysis of the crude product, content of 2,2,3,3-tetrafluorooxethane as the desired product was found 51.7 wt.%. By purification of the crude product by distillation, 592 g (purity: 95%) of fractions having boiling points of 27° to 29° C. under the normal pressure was obtained. The TFE conversion-based yield was 39.3%.

$^{19}$NMR(CFCl$_3$ basis):

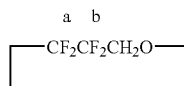

a −78.4 ppm
b −118.0 ppm
$^1$H-NMR:

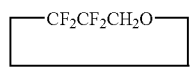

δ 4.89 ppm(2H, t, J=10.2 HZ)

Example 2

In Example 1, the amount of trifluoroacetic acid was changed from 800 g to 400 g, whereby 570 g (purity: 93 wt. %) of 2,2,3,3-tetrafluorooxethane was obtained. The TFE conversion-based yield was 37.1%.

Example 3

In Example 1, 800 g of 2,2,3,3,3-pentafluoropropyltrifluoroacetic acid ester CF$_3$COOCH$_2$CF$_2$CF$_3$ was used in place of trifluoroacetic acid, whereby 960 g (tetrafluorooxethane content: 55.6 wt. %) of crude product was obtained. By purification of the crude product by distillation, 524 g (purity: 96%) of 2,2,3,3-tetrafluorooxethane was obtained, and the TFE conversion-based yield was 35.2%.

Example 4

In Example 1, 800 g of 2,2,2-trifluoroethyltrifluoroacetic acid ester CF$_3$COOCH$_2$CF$_3$ was used in place of trifluoroacetic acid, whereby 982 g (tetrafluorooxethane content: 56.8 wt. %) of crude product was obtained. By purification of the crude product by distillation, 540 g (purity: 95%) of 2,2,3,3-tetrafluoro-oxethane was obtained, and the TFE conversion-based yield was 35.9%.

Comparative Example

In Example 1, no trifluoroacetic acid was used, whereby 279 g (purity: 94 wt. %) of 2,2,3,3,-tetrafluorooxethane was obtained and the TFE conversion-based yield was 18.3%.

The invention claimed is:

1. A process for producing 2,2,3,3-tetrafluorooxethane, which comprises allowing tetrafluoroethylene to react with paraformaldehyde in anhydrous hydrogen fluoride, said reaction being carried out in the presence of polyfluoroalkylcarboxylic acid or polyfluoroalkyl ester thereof: represented by the following formula:

RfCOORf' wherein Rf is a polyfluoroalkyl group having 1-5 carbon atoms, and Rf' is a hydrogen atom or a polyfluoroalkyl group having 1-5 carbon atoms.

2. A process for producing 2,2,3,3-tetrafluorooxethane according to claim 1, wherein the carboxylic acid, represented by the formula RfCOORf', is CF$_3$COOH.

3. A process for producing 2,2,3,3-tetrafluorooxethane according to claim 1, where the carboxylic acid ester, represented by the formula RfCOORf', is CF$_3$COOCH$_2$CF$_2$CF$_3$.

4. A process for producing 2,2,3,3-tetrafluorooxethane according to claim 1, where the carboxylic acid ester, represented by the formula RfCOORf', is CF$_3$COOCH$_2$CF$_3$.

5. A process for producing 2,2,3,3-tetrafluorooxethane, which comprises allowing tetrafluoroethylene to react with trioxane in anhydrous hydrogen fluoride, said reaction being carried out in the presence of polyfluoroalkylcarboxylic acid or polyfluoroalkyl ester thereof represented by the following formula:

RfCOORf' wherein Rf is a polyfluoroalkyl group having 1-5 carbon atoms, and Rf' is a hydrogen atom or a polyfluoroalkyl group having 1-5 carbon atoms.

6. A process for producing 2,2,3,3-tetrafluorooxethane according to claim 5, wherein the carboxylic acid, represented by the formula RfCOORf', is CF$_3$COOH.

7. A process for producing 2,2,3,3-tetrafluorooxethane according to claim 5, where the carboxylic acid ester, represented by the formula RfCOORf', is CF$_3$COOCH$_2$CF$_2$CF$_3$.

8. A process for producing 2,2,3,3-tetrafluorooxethane according to claim 5, where the carboxylic acid ester, represented by the formula RfCOORf', is CF$_3$COOCH$_2$CF$_3$.

* * * * *